United States Patent [19]

Huebner

[11] Patent Number: 5,662,649
[45] Date of Patent: Sep. 2, 1997

[54] EXTERNAL FIXATOR FOR REPAIRING FRACTURES OF DISTAL RADIUS AND WRIST

[76] Inventor: Randall J. Huebner, 18560 S.W. Hart Rd., Aloha, Oreg. 97007

[21] Appl. No.: 636,326

[22] Filed: Apr. 22, 1996

Related U.S. Application Data

[63] Continuation-in-part of Ser. No. 389,056, Feb. 15, 1995, Pat. No. 5,545,162.

[51] Int. Cl.$^6$ ................................................. A61B 17/60
[52] U.S. Cl. ................................ 606/57; 606/54; 606/59; 606/105
[58] Field of Search ............................... 606/54, 55, 57, 606/58, 59, 105

[56] References Cited

U.S. PATENT DOCUMENTS

| | | |
|---|---|---|
| 583,455 | 6/1897 | Bush . |
| 1,201,864 | 10/1916 | Overmeyer . |
| 1,789,060 | 1/1931 | Weisenbach . |
| 2,214,490 | 9/1940 | Thomas . |
| 2,250,417 | 7/1941 | Ettinger . |
| 2,251,209 | 7/1941 | Stader . |
| 2,333,033 | 10/1943 | Mraz . |
| 2,371,519 | 3/1945 | Haynes . |
| 2,391,537 | 12/1945 | Anderson . |
| 2,391,693 | 12/1945 | Ettinger . |
| 2,393,694 | 1/1946 | Kirschner . |
| 2,393,831 | 1/1946 | Stader . |
| 2,393,982 | 2/1946 | Giesen . |
| 2,406,987 | 9/1946 | Anderson . |
| 2,434,431 | 1/1948 | Pincock . |
| 2,435,850 | 2/1948 | Siebrandt . |
| 2,443,106 | 6/1948 | Grosso . |
| 2,697,433 | 12/1954 | Zehnder . |
| 3,128,768 | 4/1964 | Geistauts . |
| 3,244,170 | 4/1966 | McElvenny . |
| 3,835,849 | 9/1974 | McGuire . |
| 3,862,631 | 1/1975 | Austin . |
| 3,961,854 | 6/1976 | Jaquet . |
| 3,975,032 | 8/1976 | Bent et al. . |
| 4,003,096 | 1/1977 | Frey . |
| 4,040,130 | 8/1977 | Laure . |
| 4,096,857 | 6/1978 | Cramer et al. . |
| 4,127,119 | 11/1978 | Kronner . |
| 4,135,505 | 1/1979 | Day . |
| 4,220,146 | 9/1980 | Cloutier . |
| 4,244,360 | 1/1981 | Dohogne . |

(List continued on next page.)

FOREIGN PATENT DOCUMENTS

| | | |
|---|---|---|
| 24 37 752 | 2/1976 | Germany . |
| 27 45 504 | 4/1979 | Germany . |
| 36 14 305 | 11/1987 | Germany . |
| 2 086 231 | 5/1982 | United Kingdom . |

OTHER PUBLICATIONS

"Distal Radius Fractures," by John M. Agee, MD, *External Fixation*, vol. 9, No. 4, Nov. 1993, pp. 577–585.

*Primary Examiner*—Michael Buiz
*Assistant Examiner*—Daphna Shai
*Attorney, Agent, or Firm*—Kolisch, Hartwell, Dickinson, McCormack & Heuser

[57] ABSTRACT

The present invention is a bone fixator for repairing fractures of the distal radius and wrist. It includes, in the preferred embodiment, at least two generally parallel, spaced-apart elongate distal mounting pins with lower ends for mounting in the metacarpal bone and at least two generally parallel, spaced-apart elongate radial mounting pins with lower ends for mounting in the radius. A distal pin clamp assembly secures the distal pins to an elongate distal member. The clamp assembly and pins are movably coupled to the distal member for translational movement along its elongate axis and pivotal motion about a pivot axis generally perpendicular to the elongate axis of the distal member and the elongate axes of the distal pins. A pin mounting carriage holds the radial pins and an elongate medial assembly is connected at one end to the pin mounting carriage for independent translational motion along an axis generally perpendicular to the elongate axes of the proximal mounting pins and the elongate axis of the medial assembly and coupled at the opposed end through a ball joint to the distal member.

21 Claims, 6 Drawing Sheets

U.S. PATENT DOCUMENTS

| | | |
|---|---|---|
| 4,271,832 | 6/1981 | Evans et al. . |
| 4,299,212 | 11/1981 | Goudfrooy . |
| 4,308,863 | 1/1982 | Fischer . |
| 4,338,927 | 7/1982 | Volkov et al. . |
| 4,349,017 | 9/1982 | Sayegh . |
| 4,393,868 | 7/1983 | Teague . |
| 4,409,970 | 10/1983 | Carrel . |
| 4,475,546 | 10/1984 | Patton . |
| 4,488,542 | 12/1984 | Helland . |
| 4,548,199 | 10/1985 | Agee . |
| 4,611,586 | 9/1986 | Agee et al. . |
| 4,628,919 | 12/1986 | Clyburn . |
| 4,922,896 | 5/1990 | Agee et al. . |
| 4,988,349 | 1/1991 | Pennig . |
| 5,254,078 | 10/1993 | Carter et al. . |
| 5,304,177 | 4/1994 | Pennig . |
| 5,320,622 | 6/1994 | Faccioli et al. . |
| 5,320,623 | 6/1994 | Pennig . |

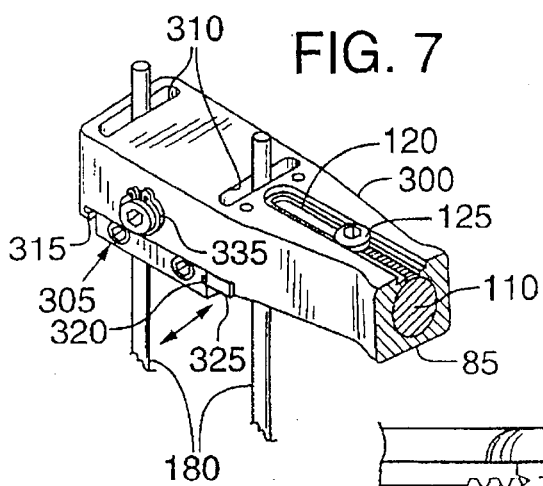
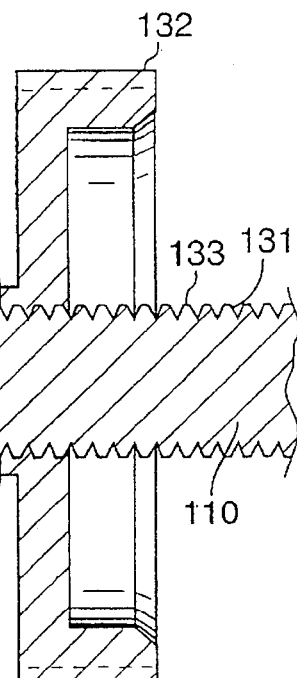
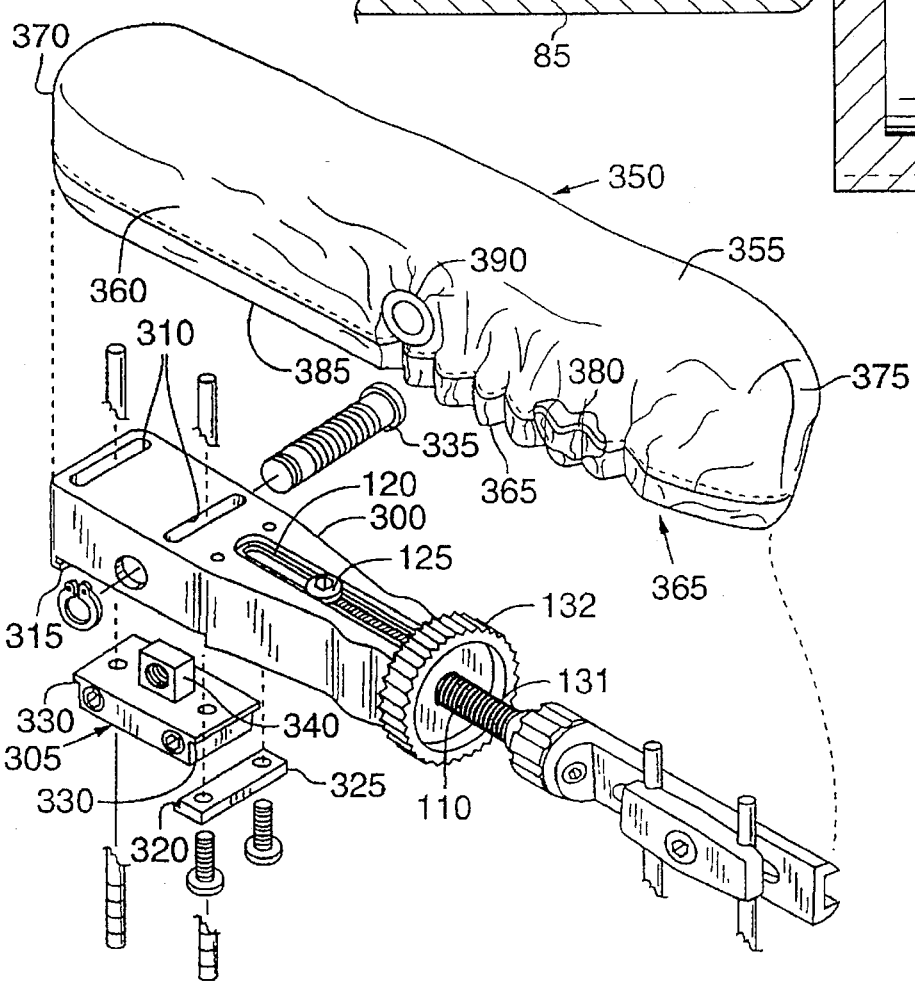

EXTERNAL FIXATOR FOR REPAIRING FRACTURES OF DISTAL RADIUS AND WRIST

CROSS-REFERENCE TO RELATED APPLICATION

This application is a continuation-in-part of U.S. patent application Ser. No. 08/389,056 filed Feb. 15, 1995 now U.S. Pat. No. 5,545,162.

FIELD OF THE INVENTION

This invention relates generally to a bone fixator for repairing fractures of the distal radius and wrist. More particularly, the invention is adapted to reduce and stabilize the relative positions of the fractured bone at the fracture site to promote proper healing and recovery.

BACKGROUND

The first external fixator was developed in 1843 for reducing and maintaining patellar fractures. Since then a large number of different fixators have been invented for splinting various bone fractures. Virtually all of these fixators have some features in common. In particular, they rely on transcutaneous pins or screws secured in the bone on either side of the fracture site. An external mechanism is attached to the pins and allows their relative positions to be adjusted. This enables the surgeon to reestablish alignment of the bone pieces at the fracture site. Once the bone is properly set, the articulations in the fixator are locked in place to maintain the chosen alignment.

The principal variations among the many fixator designs are the number of degrees of freedom provided and the relative independence of each articulation, both mechanical and geometric. The first fixator, for instance, was adjustable only in length and squeezed the fracture together by gripping opposed ends of the patella. Fixators designed to repair central fractures of the long bones typically have relatively few articulations or degrees of freedom. In contrast, fixators adapted to treat fractures of bones in the neighborhood of joints must provide many more degrees of freedom. Where there is not room to place the pins in the fractured bone between the fracture and the joint, the additional degrees of freedom are necessary because alignment must be established using pins placed in a bone on the far side of the joint from the fracture. For treatment of fractures near joints such as the wrist, which can rotate, flex and abduct, the fixator should offer some equivalent adjustment to accommodate the flexibility of the skeletal joint to allow the surgeon to establish the proper fracture alignment using forces transmitted through the joint.

Modern fixators tend to provide a large number of articulations of varying kinds. Probably the most common articulation is the ball joint. A ball joint provides one rotational and two pivotal degrees of freedom. A single setscrew or other locking mechanism can fix all three degrees of freedom simultaneously. The disadvantage of this type of articulation is that it is not possible to loosen the joint for motion in only one of the degrees of freedom without loosening it to move in other degrees of freedom. Thus, a surgeon cannot loosen the ball joint slightly to pivot it a small amount in one direction without the possibility of introducing changes affecting the other pivot and rotation settings.

In order to overcome this limitation, some fixators eliminate ball joints and rely instead on a combination of independent articulations to provide the necessary flexibility. The benefit of such a system is that each degree of freedom is mechanically independent of every other degree of freedom. A surgeon can thereby adjust the position of a single articulation in the fixator without affecting the settings of other articulations. Unfortunately, a given geometric readjustment of the bone ends at the fracture site may not correspond to an adjustment of any single articulation. Proper readjustment may require the surgeon to adjust several separate articulations, eliminating much of the benefit of independent articulations. Moreover, movement of one articulation may change some alignment of the bone ends previously established by another articulation.

With single degree of freedom articulations, such as simple pivots or slides, there are two basic adjustment techniques: gear-driven and free. Free articulations are typically freely adjustable until some type of lock is applied to secure the articulation at a selected setting. When the lock is loosened, the articulation is relatively free to move as the surgeon applies force to the joined members. Gear-driven articulations, in contrast, move under the control of some adjustment mechanism which provides mechanical advantage, such as a worm gear and rack or similar structure. Turning the worm gear causes the articulation to move incrementally in accordance with the rotation of the worm gear. This latter type of articulation generally provides the surgeon greater precision and control when making fine adjustments, bat hinders rapid gross corrections. It is possible to provide an articulation having both properties; however, in order to allow free motion of the articulation, the mechanical advantage provided by the gear reduction must be rather minimal. This would reduce the precision of the adjustment and negate the very purpose for which a gear drive would be used in the first place.

Most fixators also include some type of extensible/contractible articulation to permit the longitudinal spacing between the pins on opposite sides of the fracture to be controlled. This type of translational freedom can be used to accommodate individuals of varying size, as well as to distract the fracture, if necessary. In addition, for general purpose fixators which are not designed for a specific fracture, translational degrees of freedom can be used to create whatever spacing is required on either side of the fracture to allow for proper pin placement.

Fixators may be either general purpose or fracture specific. General purpose fixators are designed with considerable flexibility to accommodate many different types of fractures whereas fixators intended for use on a specific type of fracture typically have fewer degrees of freedom. In addition, the articulations provided are usually tailored to correct for specific fracture displacements. Likewise, for fractures too close to a joint to permit pin placement on both sides of the fracture, the articulations are adapted to compensate for varying joint position. Articulations corresponding to joint movements may also be used to set the joint in a comfortable position, as well as align the ends of the bone at the fracture site.

One of the more common fractures requiring a fixator for proper treatment is a fracture of the distal radius, or Colles fracture. This type of fracture usually results from a fall on an outstretched hand. The fracture line is usually quite close to the distal head of the radius and, because of the lack of space and the number of tendons and nerves in the area, it is not possible to mount pins in the radius on the distal side of the fracture. Therefore, such fractures are reduced using a pair of pins set in the metacarpal bone and a pair of pins set in the radius on the proximal side of the fracture. In order to avoid damage to tendons and nerves, the radial pins are usually set in the third quarter of the radius, i.e., the proximal half of the distal half of the radius. Since the pins are set on opposite sides of the wrist joint, the fixator must be sufficiently articulated to reduce the fracture using forces transmitted through the wrist joint.

The wrist joint permits the hand to move in three-degrees of freedom relative to the forearm. First, the hand can move in supination and pronation, i.e., the rotation about the longitudinal axis of the forearm. Second, the hand can move in adduction and abduction, i.e., pivoting about an axis perpendicular to the plane of the palm. The last type of mobility of the hand is flexion and extension, which is the pivotal motion about an axis in the plane of the palm and perpendicular to the longitudinal axis of the forearm.

An example of a fixator designed for the treatment of Colles fractures is disclosed in U.S. Pat. No. 4,992,896 to Agee et at. (Agee '896). In operation, the device is mounted on two pairs of pins as described above. The first pair of pins is carried by a metacarpal bar mounted in a trolley so that it can pivot about an axis parallel to the axes of the pins, as well as translate toward and away from the trolley along the same axis. The translational position of the bar relative to the trolley is controlled by a gear drive and the pivotal motion is a free articulation with a lock.

The trolley is movably mounted to an elongate distal element and is positioned along distal element using a rack and coacting worm gear. The distal member is joined to a second element through a pivot joint having an axis that forms an acute angle with the longitudinal axis of the distal element. The second element is in turn coupled to a third element by a pivot joint. The second pair of pins is mounted in the third element, and both the pivotal axes connecting the second element to adjacent elements intersect the distal pin of the second pair. The pivot axis between the second and third elements is specifically coaxial with the axis of the distal pin. Both pivotal joints are gear-driven using worm gear/rack mechanisms.

Of the five-degrees of freedom provided by the Agee '896 fixator, four are gear-driven articulations, rather than free moving. The large proportion of gear-driven articulations in Agee makes the fixator relatively easy to fine tune once it is place, but also make it more difficult to initially install. The first step in the process of installing the fixator on the patient is placing the pairs of pins in the metacarpal and radius. After the location of the pins is established and they are installed in the bones, the surgeon installs the fixator over the free ends of the pins. Because most of the articulations in the Agee '896 fixator are gear driven, the surgeon must carefully preset each fixator articulation to match the pin placement. If the articulations were free moving, the surgeon could simply loosen the locks and then flex and move the articulations as necessary to fit the pin placement.

An additional disadvantage of the Agee '896 fixator is the requirement that the axes of the pins all be substantially parallel. This is necessary because the Agee '896 patent does not have an articulation to fully accommodate the pin axes in the metacarpal being misaligned with the pin axes in the radius. The pin misalignment could be in either of two forms—abduction or supination. Since the metacarpal bar pivots freely about an axis generally parallel with flexion pivot axis of the wrist, misalignment in this direction is not critical. A slight misalignment in supination can be compensated for by using the pivot articulation between the distal and second elements. However, because the two pivot articulations between the second element and adjacent elements have only a small range of motions, approximately 15–20-degrees on either side of neutral, if the pivots must be adjusted to compensate for supination pin misalignment, there may not be sufficient travel left to properly reduce the fracture. There is no adjustment whatsoever for accommodating abduction misalignment.

Another deficit resulting from the lack of adequate supination and abduction flexibility in the Agee '896 fixator is the inability to set the wrist joint to a comfortable resting position in some cases. The resting position of a relaxed wrist is about 14-degrees extended and about 15-degrees abducted. While the Agee '896 fixator provides adequate flexion range, it does not provide any adjustment for abduction, thus forcing the metacarpal into parallel alignment with the radius—some 15-degrees away from the resting position.

Another drawback to the Agee '896 fixator is that the pivot axis of the flexion articulation of the metacarpal bar does not correspond to the pivot axis of the flexion of the wrist. Thus adjusting the flexion using the metacarpal bar pivot will disrupt alignment of the bone ends at the fracture site.

In addition to the requisite physical characteristics of a fixator, it is important to consider the psychological impact of the fixator on the patient. The sight of pins passing through the wearer's skin can be distressing to the wearer, as well as other people who may come into contact with the wearer. This may be particularly true during meals and in public. It is therefore desirable to mitigate the deleterious psychological impact of wearing a fixator, to whatever extent possible.

It is therefore an object of the present invention to provide a fixator for use on fractures of the distal radius or wrist.

It is another object of the present invention to provide a fixator for use on fractures of the distal radius that is articulated to allow adjustment of each of the three-degrees of freedom of the wrist.

It is an additional object of the present invention to provide a fixator, for use on fractures of the distal radius, that provides a sufficient range of mobility to accommodate wrist flexibility and imprecise pin placement and still have enough travel left to reduce the fracture.

It is yet another object of the present invention to provide a fixator for use on fractures of the distal radius with enough free articulations to facilitate easy mounting on the support pins after they are installed in the radius and metacarpal bones.

An additional object of the present invention is to provide a fixator for use on fractures of the distal radius that allows the surgeon to achieve accurate and rapid reduction of the fracture.

One more object of the present invention is to provide a fixator including an enveloping cover to make the fixator more cosmetically acceptable.

These and other objects and advantages will be more clearly understood from a consideration of the accompanying drawings and the following description of the preferred embodiment.

SUMMARY OF THE INVENTION

The present invention is a bone fixator for repairing fractures of the distal radius and wrist. It includes, in the preferred embodiment, at least two generally parallel spaced-apart elongate distal mounting pins with lower ends for mounting in the metacarpal bone and at least two generally parallel spaced-apart elongate radial mounting pins with lower ends for mounting in the radius. A distal pin clamp assembly secures the distal pins to an elongate distal member. The clamp assembly and pins are movably coupled to the distal member for translational movement along its elongate axis and pivotal motion about a pivot axis generally perpendicular to the elongate axis of the distal member and the elongate axes of the distal pins. The fixator further includes a proximal pin mounting block for securing the radial pins and an elongate medial assembly of adjustable length. The medial assembly is pivotally connected at one end to the pin mounting block for independent pivotal motion about an axis generally parallel to the elongate axes of the proximal mounting pins and coupled at the opposed end through a ball joint to the distal member.

In an alternative embodiment, a pin carriage block holds the radial pins and is coupled to the medial assembly for independent translational motion perpendicular to the axis of the pins and the longitudinal axis of the radius. In addition or alternatively, the medial assembly may include a mechanically driven extension/distraction mechanism.

BRIEF DESCRIPTION OF THE DRAWINGS

FIG. 7 is a perspective view of the proximal end of an alternative embodiment of a fixator according to the present invention.

FIG. 8 is a perspective, partially exploded view of the fixator of FIG. 7.

FIG. 9 is a partial cross-sectional view of a portion of the fixator of FIGS. 7 and 8.

DETAILED DESCRIPTION OF THE PREFERRED EMBODIMENT

Figure 1:
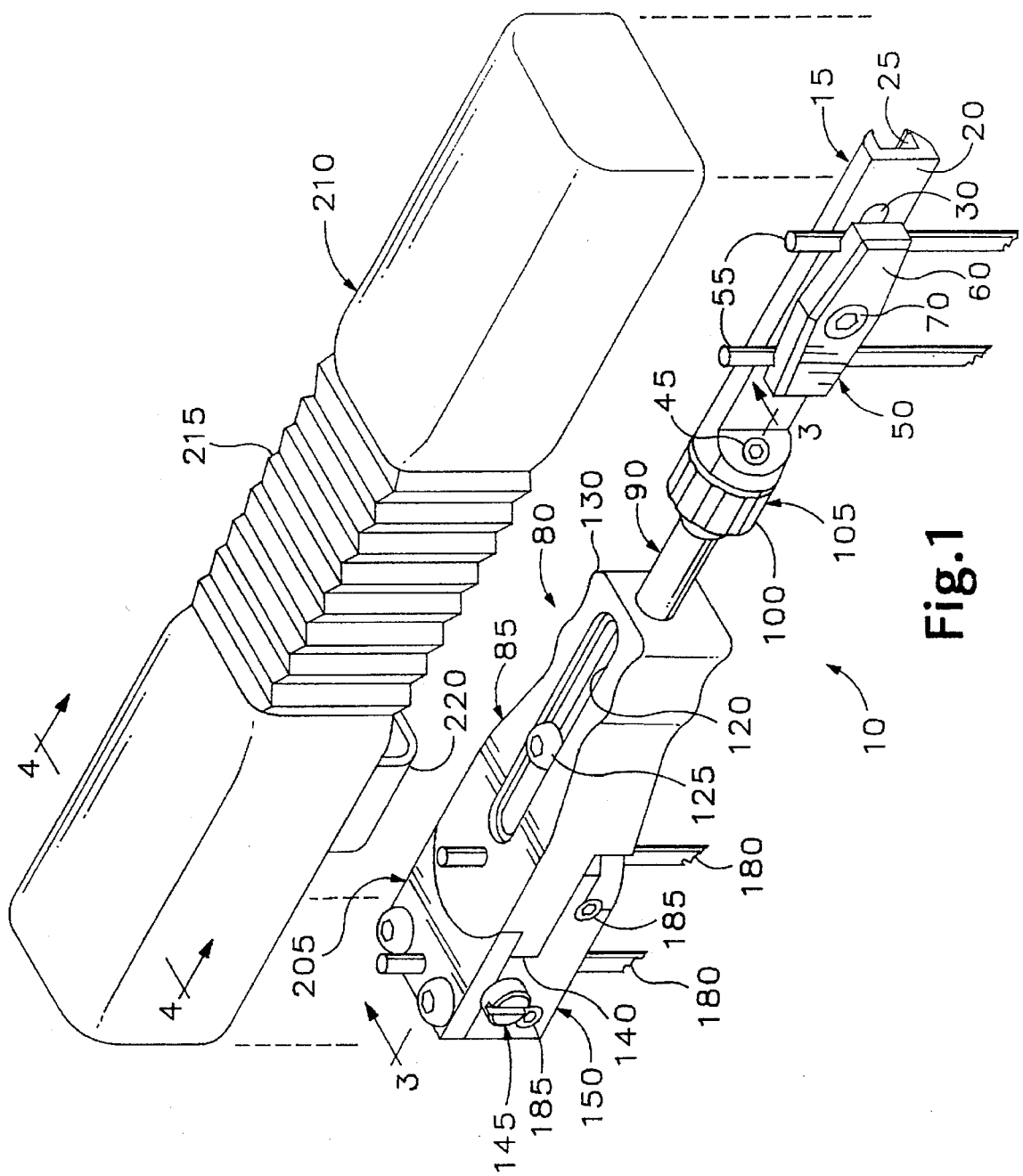
FIG. 1 is a perspective view of a fixator and cover according to the present invention.
Figure 2:
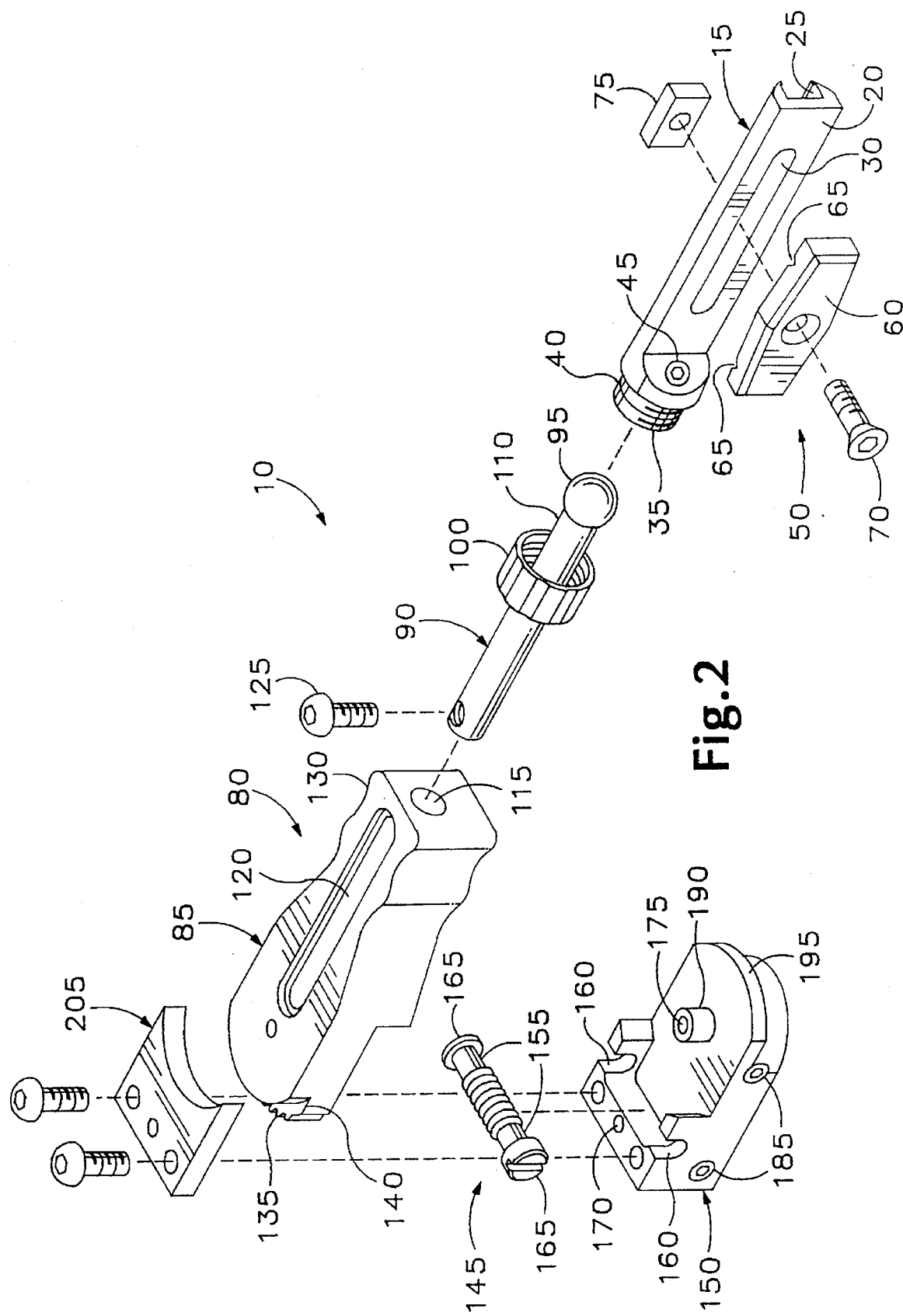
FIG. 2 is an exploded perspective view of the fixator of FIG. 1.
Figure 3:
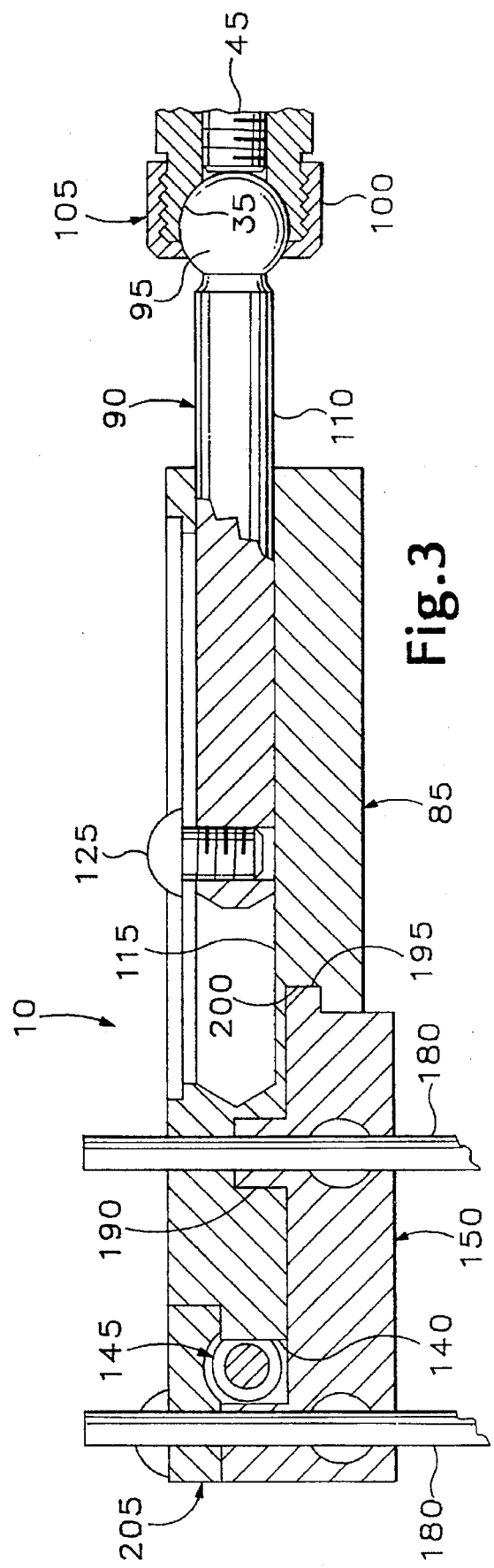
FIG. 3 is a cross-sectional view along line 3—3 in FIG. 1.

A fixator according to the present invention is shown generally at 10 in FIGS. 1 and 2. An elongate distal member 15 forms the distal end of fixator 10. A generally planar pin shelf 20 and opposed nut track 25 extend along the length of distal member 15. An elongate slot 30 extends along distal member 15, forming a passage between track 25 and shelf 20. At the proximal terminus of distal member 15 is a semi-spheroidal cup 35 with externally threaded walls 40. See FIG. 3. A setscrew 45 extends through a portion of distal member 15 into the bottom of cup 35. The axis of setscrew 45 is aligned to intersect with the center of the sphere defined by cup 35.

A pin clamp assembly 50 secures two distal pins 55 to distal member 15. Pin clamp assembly 50 includes a clamp plate 60 with a transverse groove 65 formed at either end to receive distal pins 55. Clamp plate 60 is urged against shelf 20 by a clamp screw 70 which extends through slot 30 and into nut track 25. Clamp screw 70 is engaged in a pin clamp nut 75 which rides in nut track 25. When clamp screw 70 is tightened, clamp nut 75 is urged against the bottom of nut track 25 and clamp plate 60 is urged against shelf 20 thereby trapping pins 55 between clamp plate 60 and shelf 20.

When clamp screw 70 is loosened, pin clamp assembly 50 is free to travel back and forth along the length of distal member 15, limited only by the extent of nut track 25 and slot 30. Clamp plate 60 can additionally pivot about clamp screw 70. These motions allow pins 55 to be positioned as desired along distal member 15, as well as pivoted in the plane of shelf 20 about the axis of clamp screw 70.

An elongate medial assembly 80, including an elongate medial block 85 and a ball rod 90 is coupled to distal member 15 by a ball 95 at the distal end of ball rod 90. Ball 95 fits in cup 35 and is retained therein by a ball joint cap 100 to form a ball joint 105. Ball joint cap 100 is internally threaded and screws down over externally threaded walls 40. When cap 100 is fully seated over cup 35, ball joint 105 should still move relatively freely, allowing ball rod 90 to be positioned anywhere within a cone with an apex at the center of ball 95 and a side angle of approximately 20–30-degrees from the axis of distal member 15. Ball rod 90 can also be rotated about its axis without restriction in ball joint 105. Setscrew 45 fixes the orientation of ball joint 105 when tightened. If setscrew 45 is only lightly tightened, it will create some drag on the motion of ball joint 105, while still allowing some movement.

Ball 95 is mounted on a shaft 110, which is in turn telescopically engaged in a longitudinal bore 115 in medial block 85 to make medial assembly 80 adjustable in length. An elongate aperture 120 opens onto bore 115 from the upper surface of medial block 85. A setscrew 125 mounted in the proximal end of shaft 110 slides in aperture 120 and serves to lock ball rod 90 in place when desired. Setscrew 125 also prevents ball rod 90 from rotating in bore 115. A grip 130 is incorporated in medial block 85 generally over bore 115 to accommodate the surgeon's fingers.

In an alternative embodiment, shown in FIGS. 7 and 8, shaft 110 includes threads 131 formed along its outer surface. A knurled nut 132 fits over thread 131 between ball 95 and the distal end of medial block 85. When the nut is adjacent to the block, further rotation of the nut toward the block causes the ball rod to be extended from the bore. This gives the surgeon the ability to precisely control the distraction of the fracture. Another benefit of the embodiment shown in FIGS. 7 and 8 is that the nut can be quickly spun up to the ball, allowing the telescopic adjustment of the fixator to be freely adjusted for attachment to the pins, while retaining the precision of a mechanical adjustment during reduction of the fracture. It should be noted that, in the preferred embodiment, thread 131 has a flattened crest 133 to allow it to slide more freely in bore 115. See FIG. 9.

The proximal end of medial block 85 includes an arcuate rack 135 formed on the end of a protruding ledge 140. Arcuate rack 135 co-acts with a worm gear 145 to control the position of a proximal pin mounting block 150, which is pivotally connected to medial block 85. Worm gear 145 includes bearing surfaces 155 near each end that ride in a pair of U-shaped guides 160 formed in pin mounting block 150. A flared head 165 at each end prevents worm gear 145 from moving side-to-side in pin mounting block 150.

Proximal and distal transverse openings 170, 175 extend through pin mounting block 150 to receive a pair of radial pins 180. Each transverse opening 170, 175 includes an associated setscrew 185 to secure radial pins 180. A pivot guide 190 surrounds the upper portion of distal opening 175 and medial block 85 fits over and pivots around pivot guide 190. An arcuate lip 195 on the distal end of pin mounting block 150 is received in a matching pivot slot 200 in medial block 85. See FIG. 3. The interaction of lip 195 in pivot slot 200 helps to secure medial block 85 to pin mounting block 150. A retainer plate 205 is screwed to the proximal end of pin mounting block 150 and extends over ledge 140 to further secure medial block 85 to pin mounting block 150.

An alternative embodiment of the proximal end of the present invention is shown in FIGS. 7 and 8. In the fixator of FIGS. 7 and 8, a medial block 300 extends back to the proximal end of the fixator, thus eliminating pin mounting block 150. Medial block 300 includes a pair of transverse slots 310 through which radial mounting pins 180 extend. Slots 310 allow the pins to be shifted in the dorsal or palmar direction by approximately three-eighths of an inch from center. The pins are carried by a pin mounting carriage 305 which replaces pin mounting block 150.

It should be noted that one of the advantages of the design of medial block 300 is that it can be manufactured from radiolucent materials, preferably Ultem™. Use of radiolucent materials is beneficial because the surgeon can take X-rays from angles that would otherwise be obstructed by the medial block if it were not radiolucent.

Carriage 305 mounts to the lower surface of medial block 300 and rides on a pair of projecting ledges 315, 320. Ledge 315 is formed on block 300 and ledge 320 is formed on a retention plate 325 that is screwed to the bottom of the block. Carriage 305 includes a flange 330 at each end to engage the ledges. The carriage is conveyed dorsally and laterally by a lead screw 335 is rotatably mounted in block 300 and extends from the dorsal to the palmar side thereof. A pedestal 340 projects upwardly from the top of carriage 305 to engage lead screw 335. When the lead screw is rotated, the pedestal and the carriage are conveyed either dorsally or palmarly on the screw, thus shifting position of the distal portions of the fixator relative to the radial pins. It should be noted that this is a pure palmar/dorsal translation with no pivotal component as occurs when medial block 85 is pivoted relative to pin mounting block 150.

Figure 4:
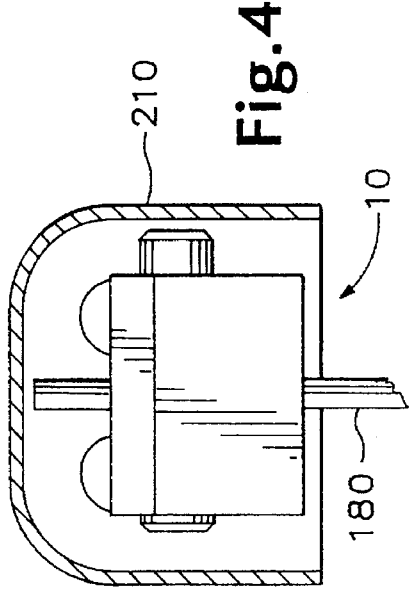
FIG. 4 is a cross-sectional view along line 4—4 in FIG. 1, showing how the cover fits over the fixator.

A cover 210 is provided to envelope and cloak fixator 10. See FIGS. 1 and 4. Cover 210 is preferably formed of thin flexible plastic. A bellows 215 in the middle of cover 210 allows the length to be adjusted to match the length of fixator 10 as installed on the patient. Although not shown, cover 210 could be formed as two telescoping pieces to achieve the same effect. A Velcro™ strap 220 or other fastener may be use to secure cover 210 to fixator 10.

An alternative cover is shown at 350 in FIG. 7. Cover 350 includes a top 355 and downwardly depending sides 360 extending around the perimeter of the top to form a cavity 365 open on one side. The cover is preferably formed of two panels of a flexible fabric material separated by a thin layer of batting. The panels are folded downward and stitched together at proximal and distal ends 370, 375, respectively, to form sides 360 and cavity 365 to enclose the fixator. An elastic band 380 is stitched into a portion of a lower edge 385 of the cover to help the cover conform to the various configurations of the fixator. A closure mechanism in the form of snap 390 is provided to join the opposed lower edges of the cover to secure it in place on a fixator.

The first step in the process of installing fixator 10 on a patient is placing distal pins 55 in the patient's metacarpal and radial pins 180 in the radius. Pins 55, 180 are installed with the aid of a drill guide, not shown, which includes two spaced-apart parallel guide holes. The drill guide insures that the two pins in each bone are parallel to one another, and generally perpendicular to the longitudinal axis of the bone.

In both locations the inter-pin spacing is about 25 mm in the preferred embodiment. The two pins in each pair should generally be as close together as possible to minimize the size of the incision required for placement and allow treatment of small patients, but they must also be far enough apart to provide adequate rigidity for reduction of the fracture.

Figure 5:
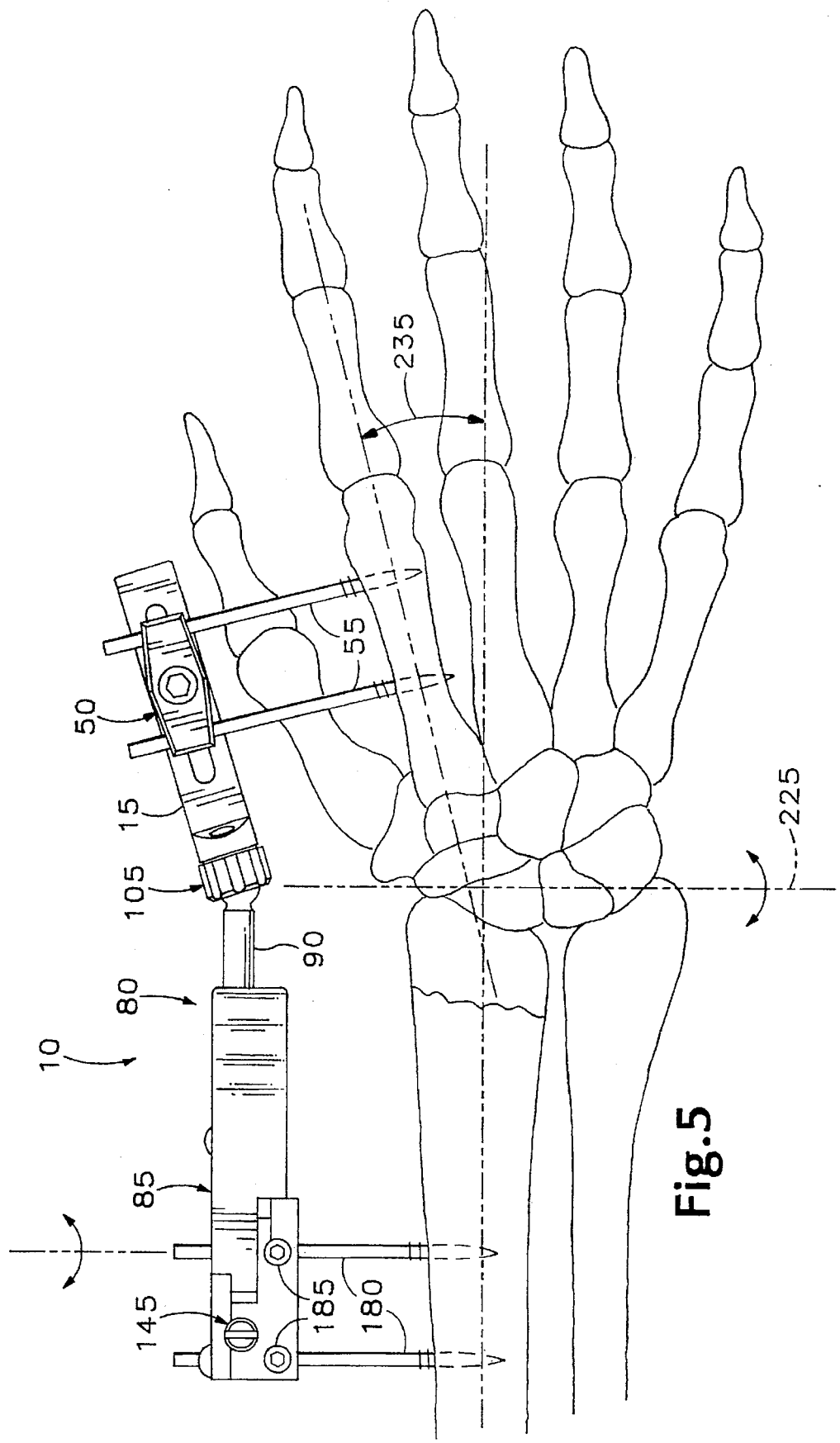
FIG. 5 is a side view of the fixator as it would be mounted on a patients arm.
Figure 6:
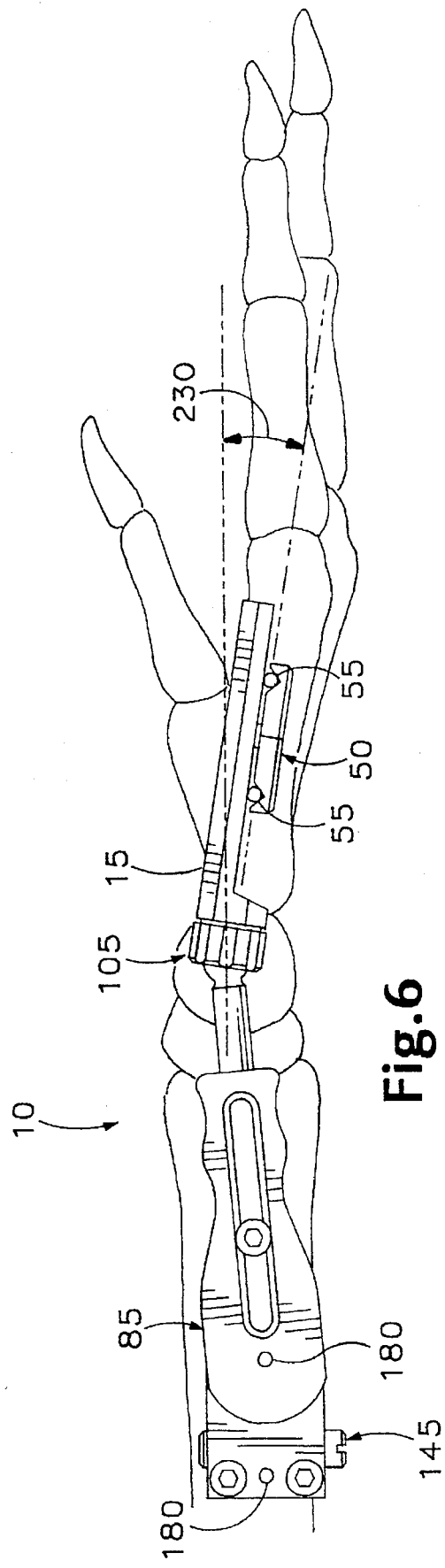
FIG. 6 is a top view of the fixator as it would be mounted on a patients arm.

After pins 55, 180 are properly installed, fixator 10 is attached. In order to place fixator 10 on pins 55, 180, it is desirable to loosen all of the free articulations so fixator 10 may be freely adjusted. With all the free articulations loosened, fixator 10 is quite limber, making the task of installing it on pins 55, 180 relatively quick and easy. Once fixator 10 is mounted on the pins, the relative positions of pin clamp assembly 50 along distal member 15 and ball rod 90 in medial block 85 are adjusted so that ball 95 is placed over the flexion/extension axis 225 of the wrist. See FIG. 5. Aligning the pivot axis of ball joint 105 with the flexion axis 225 of the wrist allows the patient's wrist to be set to the desired extension angle 230, typically 15-degrees, without disturbing the alignment of previous adjustments. See FIG. 6.

The travel of distal pins 55 along distal member 15 is used to accommodate variation in the spacing between the center of the wrist and the metacarpal, which depends on the size of the patient's hand. Medial assembly 80, similarly, telescopes to fit patients with longer or shorter forearms. Because the telescopic action of medial assembly 80 compensates for part of the variation of spacing between the distal and radial pins among individuals, the overall length of fixator 10 can reduced according to the size of the patient, making it less bulky and less likely to bump or snag on other objects around the patient than a fixator of fixed length.

The rotation of distal member 15, and therefore distal pins 55, allowed by ball joint 105 allows fixator 10 to accommodate distal and radial pins 55, 180 which are not parallel to each other. This flexibility makes alignment between distal pins 55 and radial pins 180 much less critical. The rotation also allows the supination and pronation of the patient's hand to be adjusted. As supination is adjusted, the pivot joint between medial block 85 and pin mounting block 150 must be changed to compensate for displacement of the fracture alignment since the axis of rotation of ball joint 105 is not coincident with the axis of rotation of the wrist.

The pivotal motion between distal pins 55 and distal member 15, in conjunction with displacement of distal pins 55 along distal member 15, allows the abduction angle 235 of the patient's wrist to be set to the desired value, which is typically 14-degrees. See FIG. 5. Likewise, the combined pivotal action of distal pins 55 on distal member 15 and distal member 15 on ball 95 can be used to set the radial/ulnar fracture alignment.

If distraction of the fracture is required, the length of media/assembly 80 is adjusted accordingly. This adjustment leaves ball 95 properly placed over flexion/extension axis 225 of the wrist. The dorsal/palmar alignment of the fracture site is adjusted using worm gear 145 to pivot medial assembly 80 relative to pin mounting block 150. In the alternative embodiment shown in FIGS. 7 and 8, the length of the medial assembly, and therefore distraction of the fracture, is adjusted using nut 132, which allows greater precision and control. Likewise, with the embodiment shown in FIGS. 7 and 8, the dorsal/palmar alignment is adjusted using the lead screw. This eliminates the angular movement inherent in pivoting medial assembly 80 relative to pin mounting block 150 to correct dorsal/palmar misalignment at the fracture site. As previously discussed, achieving proper reduction of fractures can be simplified if the various adjustments provided by the fixator are independent of one another.

With the exception of the pivot joint between pin mounting block 150/carriage 305 and medial block 85, each of the articulations in fixator 10 can be gradually tightened to provided increasing resistance to movement. This permits quick manual adjustment of the articulations, but otherwise holds them relatively fixed. Once the desired alignment of the fracture and wrist position are established, all of the articulations are locked in place.

It will now be dear that an improvement in this art has been provided which accomplishes the objectives heretofore set forth. While the invention has been disclosed in its preferred form, it is to be understood that the specific embodiment thereof as disclosed and illustrated herein is not to be considered in a limited sense as there may be other forms or modifications which should also be construed to come within the scope of the appended claims.

It is claimed and desired to secure by Letters Patent:

1. A bone fixator for repairing fractures of the distal radius and wrist, comprising:
   at least one elongate distal mounting pin with a lower end for mounting in the metacarpal bone;
   at least one elongate radial mounting pin with a lower end for mounting in the radius;
   an elongate distal member;
   a distal pin clamp assembly for securing the distal pin relative to the distal member;
   a proximal pin mounting carriage for securing the radial pin; and
   an elongate medial assembly connected at one end to the pin mounting carriage to allow gear-driven independent linear translational motion relative to the pin mounting carriage along an a generally perpendicular to the elongate axis of the proximal mounting pin and the elongate axis of the medial assembly and coupled articulably at an opposed end to the distal member.

2. The fixator of claim 1 wherein a lead screw connects the pin mounting carriage to the medial assembly, whereby turning of the lead screw moves the carriage relative to the medial assembly.

3. The fixator of claim 2 where the lead screw is rotatably mounted to the medial assembly and is threadedly engaged in a bore formed in the pin mounting carriage.

4. The fixator of claim 3 where the bore is formed in a pedestal formed on the pin mounting carriage.

5. The fixator of claim 2 where the medial assembly has a lower surface facing the radius and the pin mounting carriage is mounted to the medial assembly on its lower surface.

6. The fixator of claim 5 where the medial assembly includes a slot extending upward through the assembly from the lower surface and the radial pin extends through the slot.

7. The fixator of claim 1 where the medial assembly includes an elongate medial block with a longitudinal bore and a ball rod including a ball at one end and a shaft for telescopic engagement in the longitudinal bore to adjust the length of the fixator.

8. The fixator of claim 7 where the shaft of the ball rod is threaded and a distraction nut is installed over the shaft between the ball and the end of the medial block.

9. The fixator of claim 8 where the thread includes a flat crest.

10. The fixator of claim 8 where an elongate aperture opens onto the elongate bore from the exterior of the medial block and a setscrew passes through the aperture to engage the shaft and lock the position of the shaft in the bore when tightened.

11. A bone fixator for repairing fractures of the distal radius and wrist, comprising;
    at least two generally parallel, spaced-apart elongate distal mounting pins with lower ends for mounting in the metacarpal bone;
    at least two generally parallel, spaced-apart elongate radial mounting pins with lower ends for mounting in the radius;
    an elongate distal member;
    a distal pin clamp assembly for securing the distal pins relative to the distal member, the distal pin clamp assembly being movably coupled to the distal member for translational movement along the elongate axis of the distal member and pivotal motion about a pivot axis generally perpendicular to the elongate axis of the distal member and the elongate axes of the distal pins;
    a proximal pin mounting carriage for securing the radial pins; and
    an elongate medial assembly connected at one end to the pin mounting carriage to allow independent linear translational motion relative to the pin mounting carriage along an axis generally perpendicular to the elongate axes of the proximal mounting pins and the elongate axis of the medial assembly and coupled at an opposed end through a ball joint to the distal member.

12. The fixator of claim 11 where the medial assembly includes an elongate medial block with a longitudinal bore and a ball rod including a ball at one end and a threaded shaft for telescopic engagement in the longitudinal bore to adjust the length of the fixator and where a distraction nut is installed over a portion of the shaft extending out of the medial block.

13. The fixator of claim 11 wherein a lead screw connects the pin mounting carriage to the medial assembly, whereby turning of the lead screw moves the carriage relative to the medial assembly.

14. The fixator of claim 13 where the medial assembly has a lower surface facing the radius and the pin mounting carriage is mounted to the medial assembly on its lower surface.

15. The fixator of claim 14 where medial assembly includes a pair of slots extending upward through the assembly from the lower surface and the radial pins extend through the slots.

16. An apparatus for treating a fracture comprising:
    at least one distal pin adapted to be secured in a bone on one side of the fracture;
    at least one proximal pin adapted to be secured in the bone on the opposite side of the fracture from the distal pin;
    an articulated fixator mounted to the distal and proximal pins for reducing and stabilizing the fracture; and
    a fitted cover adapted to substantially envelope and fit closely about the fixator without substantially enveloping the portion of a patient's body around the fracture.

17. The apparatus of claim 16 where the cover is formed of cloth.

18. The apparatus of claim 17 where the cover is adjustable in length.

19. The apparatus of claim 18 where the cover includes an elastic section to provide adjustability in length.

20. The apparatus of claim 17 where the cover includes a top and downwardly depending sides extending around the perimeter of the top, thereby forming a cavity, and the fixator fits into the cavity.

21. The apparatus of claim 20 where the cover further includes a closure mechanism linking downwardly depending sides to retain the fixator in the cavity.

* * * * *